United States Patent [19]

Hall

[11] 4,145,813
[45] Mar. 27, 1979

[54] SYSTEM FOR SELECTIVELY SUPPLYING FLUIDS TO DENTAL AND SURGICAL TOOLS

[75] Inventor: Arthur L. Hall, Knoxville, Tenn.

[73] Assignee: Halmon-Locren Industries, Inc., Knoxville, Tenn.

[21] Appl. No.: 722,609

[22] Filed: Sep. 13, 1976

[51] Int. Cl.² ............................................. A61C 19/02
[52] U.S. Cl. ..................................... 32/22; 137/625.18
[58] Field of Search ............................. 32/22, DIG. 3; 137/625.18, 625.14, 883, 884

[56] References Cited

U.S. PATENT DOCUMENTS

| | | | |
|---|---|---|---|
| 3,578,007 | 5/1971 | Blake | 137/625.18 |
| 3,638,310 | 2/1972 | Austin | 32/22 |
| 3,673,709 | 7/1972 | Page | 32/22 |
| 3,757,421 | 9/1973 | Kraft | 32/22 |
| 3,766,943 | 10/1973 | Murata | 137/884 |
| 3,875,958 | 4/1975 | Miller | 32/22 |
| 3,886,660 | 6/1975 | Thornton et al. | 32/22 |
| 3,918,161 | 11/1975 | Morgan et al. | 32/22 |
| 3,973,583 | 8/1976 | Sorenson | 137/625.18 |

Primary Examiner—Russell R. Kinsey
Assistant Examiner—John J. Wilson
Attorney, Agent, or Firm—Luedeka & Hodges

[57] ABSTRACT

A system for selectively and controllably supplying pressurized fluids to dental or surgical tools requiring high pressure air and low pressure air and/or liquid. The fluids are selectively supplied through conduit means to a manifold including a plurality of passageways. Removably mounted upon the manifold are individual valve sets, each one associated with a tool. Each valve set is simultaneously opened or closed by the longitudinal movement of a shaft carrying spaced apart enlargements. The longitudinal movement is actuated by control air controlled by hangers upon which unused tools are hung. When a valve set is opened, fluids flow through manifold passageways, through the valve set, back through other manifold passageways and through conduit means to the selected tool.

1 Claim, 11 Drawing Figures

SYSTEM FOR SELECTIVELY SUPPLYING FLUIDS TO DENTAL AND SURGICAL TOOLS

The present invention relates generally to improvements in the art of dental and surgical equipment and more particularly to an improved apparatus for control of pressurized fluid flow to dental and surgical tools. The present invention has particular application to systems employing a plurality of tools, each of which requires supplies of a plurality of pressurized fluids.

In fields of dentistry and surgery a variety of hand tools are used, many of which require pressurized fluids. For example, drills and other cutting tools are generally driven by air turbines which are powered by a supply of high pressure air. In addition, many operations require use of lower pressure air or a liquid, such as water or saline solution, for cooling and/or keeping the working area clear.

Usually, an operator will maintain several tools in a "ready" condition, either in case a bit breaks or to perform different operations without changing bits, a time-consuming activity. Control mechanisms are generally provided to perform the functions of receiving high pressure air and pressurized liquid from the sources, splitting the air into driving air and lower pressure air, and selectively supplying the fluids to a series of valves. (Usually, each tool has an individual valve associated with it.) When the operator selects the appropriate tool and required fluids for a particular operation, he sets the control mechanism to supply the desired fluids and activates the associated valve to allow the fluids to flow to the tool. The rate of flow is generally controlled by the operator through a foot pedal, so that his hands are free to handle tools.

A variety of prior art apparatus have been used as control mechanisms. However, there have also been a variety of attendant deficiencies.

The known controls for apparatus of the class described have been extremely complex in construction and have been very difficult to repair and maintain. Essentially, in most of the prior art devices, the control of fluids has been effected by a multiplicity of diaphragm valves which are incorporated in the control. Diaphragm valves are not entirely satisfactory at high pressures and particularly at a pressure as high as 150 psi, which is required for some of the more modern surgical type tools. Breakdown of a valve or valves can make the control inoperable and repair, when the valve is incorporated with a member of other valves and elements in the system, is both time consuming and expensive. This has resulted in a substantial amount of "downtime" and relatively high maintenance costs.

It is therefore an object of this invention to provide a dental and dental surgical tool fluid supply system which can handle fluids at high pressures using a minimum of moving parts. Another object of this invention is to provide a single fluid system, which can be used for a variety of types of dental and surgical tools. A further object of this invention is to provide a unit in which the valve set for any tool can be quickly, and easily and economically replaced by the operator without the need of a trained serviceman.

Other objects and advantages of the invention will become apparent by reference to the following description and the accompanying drawings.

Figure 1:
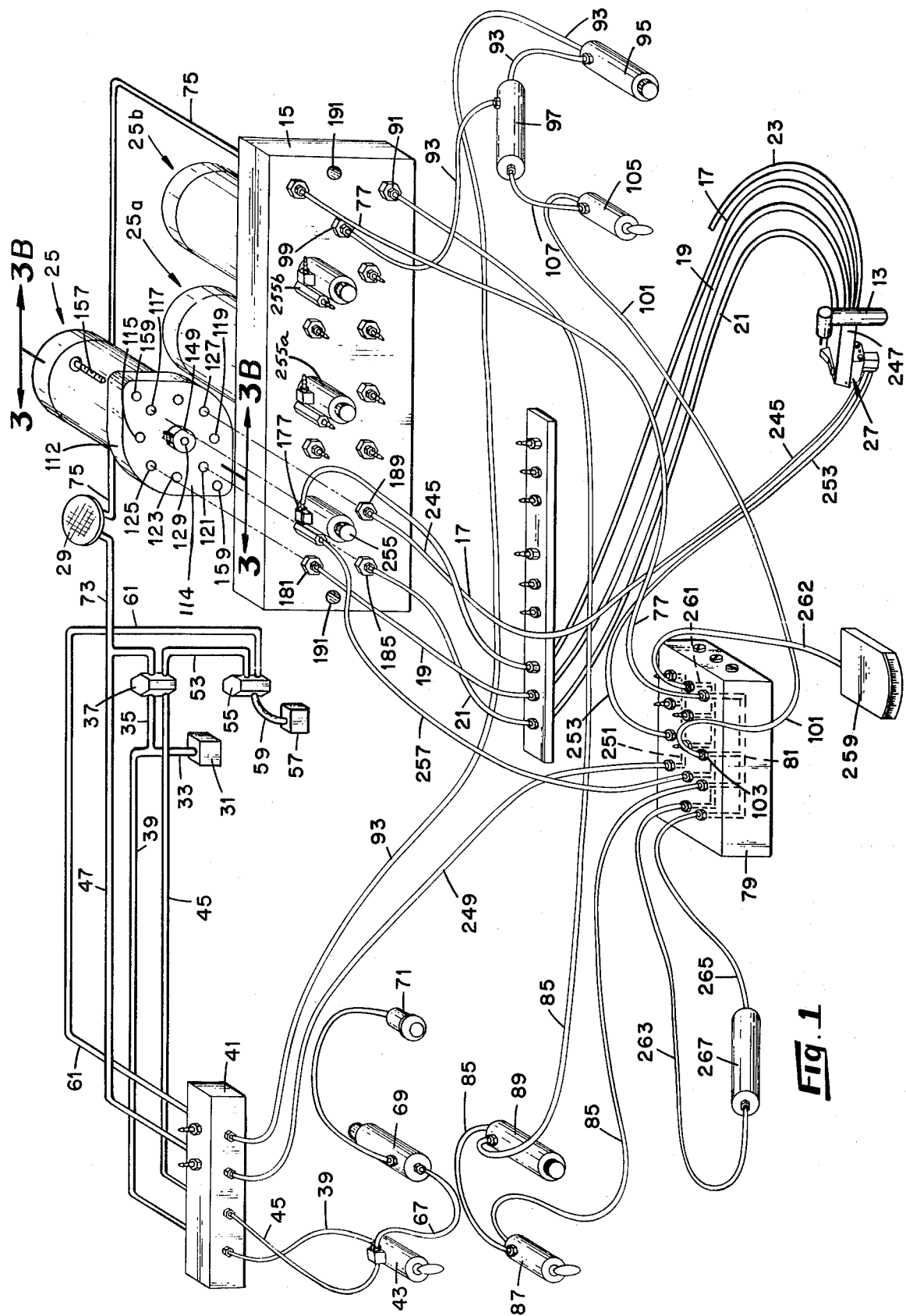
FIG. 1 is a diagrammatic view of a tool system and control means embodying various features of the invention.

The system illustrated in the drawings is adapted to operate dental and surgical tools from a supply of pressurized air. Tools of this type are driven by air turbines within the tool and include such tools as drills, and the like. Such tools, in addition to the high pressure or drive air, also include provision for dispensing a liquid such as water or saline solution to cool and lubricate the area which is being worked upon and also usually include air at low pressure which is used for various purposes such as cooling the work area, drying the work area, or clearing the area of chips. This low pressure air will be referred to hereinafter as "chip air."

Drive air is usually conducted to the tool at a pressure of from 50–150 pounds per square inch, the pressure depending upon the type of tool being employed and the speed of rotation which is desired for the tool. To this end, controls are provided for adjusting the drive air pressure for individual tools. Means are also provided in the system for selectively applying chip air and/or liquid depending upon the working conditions.

In the drawings (FIGS. 1 and 2) there is illustrated a set of three air turbine drills, 13, 13a, and 13b. In order to simplify the description, only the connections for one drill 13 will be described in detail, it being understood that the other drills 13a and 13b are connected in the same manner with the corresponding elements being identified with the same reference numbers carrying the suffix "a" or "b", respectively. Drill 13 is connected to a manifold 15 by three conduits, 17, 19, and 21, conduit 17 being adapted to supply drive air, conduit 19 being adapted to provide liquid, and conduit 21 being adapted to provide chip air. A fourth conduit 23 extends from the tool to exhaust the spent drive air from the drill 13 to a point remote from that at which the work is taking place. The manifold 15 shown in FIG. 1 is designed to accommodate three separate tools and it is within the scope of this invention to provide manifolds which accommodate any desired number of tools.

Briefly, the manifold 15 is supplied with drive air, chip air and liquid at working pressures. Control of the flow of fluids from the manifold 15 is accomplished by individual replaceable valve sets 25, 25a and 25b, which are removably attached to the manifold 15, one valve set being provided for each tool. In operation, each valve set is actuated by a source of pressure air to simultaneously supply the desired combination of drive air, chip air and liquid to its associated tool.

Actuation of any given tool is accomplished by removing the tool from its associated hanger or rest 27, 27a or 27b which readies the fluid supply to its associated tool. Activation of the tool is then accomplished through a foot pedal 29 or other activation device. Individual manually actuated controls are provided to supply chip air and/or liquid, as desired.

The system is connected to a suitable source of pressure air 31 through conduit 33. The pressure in the source is selected to be higher than the highest pressure to be supplied to the tools, taking into account the pressure drop which occurs in the system between the source of air and the tools. The conduit 33 is connected through conduit 35 to the inlet of an air actuated, normally closed control valve 37 and through conduit 39, through a junction block 41 to a manually actuated master valve 43. When the master valve 43 is manually opened, it supplies air through conduit 45 through the junction block 41 and through conduit 45 to the air operated valve 37 which is thus opened connecting the source of air 31 through conduit 47 to the junction block 41. In the conduit 47, there are provided a suitable filter 49 to remove any undesirable suspended material and a regulator 51 to control the pressure of air supplied to the system.

The pressurized air from the conduit 45 which is utilized to actuate the valve 37 is conducted through conduit 53 to an air actuated, normally closed, water valve 55. The inlet of the water valve 55 is connected to a source of pressurized water 57 through the conduit 59 and the outlet of the valve 55 is connected through conduit 61 to the junction block 41. In the conduit 61 there are provided a suitable filter 63 to remove any undesirable foreign materials from the liquid a regulator 65 to control the pressure of water supplied to the system, and an electrical heater 66 which is employed to heat the liquid to the desired temperature.

In order that there is an indicator to show whether or not the unit is being supplied with pressure air and water, the outlet of the master valve 43 is also connected by conduit 67 through a pressure reducer 69 to an air actuated indicator light 71.

In order to provide drive air to the manifold, a conduit 73 interconnects the foot pedal actuated valve 29 to the conduit 47. The valve 29 is in turn connected to the manifold 15 by the conduit 75.

In order to provide a source of chip air, a conduit 77 which communicates with the conduit 75, extends to a distribution block 79. The distributor block 79 includes an internal passageway 81 which communicates with an outlet 83 which is connected by means of a conduit 85 through a manually operated valve 87, which determines whether or not chip air is to be supplied to the system, through an air regulator 89 to the chip air inlet 91 on the manifold 15 by means of conduits 85.

In order to supply water to the manifold, the conduit 61 at the junction block 41 is connected by means of a conduit 93 including a pressure regulator 95 and an air actuated valve 97 to the water inlet 99 on the manifold 15. Control of the supply of water is effected by the air actuated valve 97. This control is effected by air from an air conduit 101, having one end connected to an outlet 103 in the distributor block which in turn communicates with the air passageway 81. The other end of the conduit 101 is connected to the inlet of a manually actuated air valve 105 whose outlet communicates with the air inlet on the control valve 97 through conduit 107.

The manifold 15 serves as a mounting surface for the valves 25, 25a and 25b and as conduit means to and from the valves 25, 25a and 25b for water, chip air, drive air and pilot air (also called "control air" because it is used to control the valves). The manifold 15 is essentially a unitary block formed by three sealably joined sections, a mounting section 109, a middle section 111, and a face section 113.

The valves 25, 25a and 25b are identical so that only one, 25, will be described, the corresponding parts on the valves 25a and 25b will be given the same reference numerals with the suffixes "a" and "b", respectively. Valve 25 includes a base 112 having a mounting face 114 which is adapted to engage the mounting section 109 of the manifold 15. Provided in the valve mounting face 14 are a drive air inlet 115, a drive air outlet 117, a chip air inlet 119, a chip air outlet 121, a water inlet 123, a water outlet 125, a pilot air inlet 127 and a pilot air outlet 129. The manifold mounting section 109 is provided with a mounting face 131 which is correspondingly provided with a drive air outlet 133, a drive air inlet 135, a chip air outlet 137, a chip air inlet 139, a water outlet 141, a water inlet 143, a pilot air outlet 145 and a pilot air inlet 147. The inlets and outlets on the mounting face 131 of the mounting section 109 and the mounting face 114 on the valve 25 are arranged in mirror image patterns so that when the valve 25 is mounted, the corresponding inlets and outlets meet. In order to insure proper alignment of the inlets and outlets on the mounting faces 114 and 131, a boss 149 is provided centrally of the mounting face 113 of the valve 25, the boss 149 being provided with a key 151 which engages a keying slot 153 in the pilot air inlet 147 of the mounting face 131.

Provided in the manifold mounting section 109 are a pair of screw mounting holes 155 into which mounting screws 157 may be threaded to secure the valve 25 by corresponding mounting holes 159 in the base 112 of the valve 25.

Figure 11:
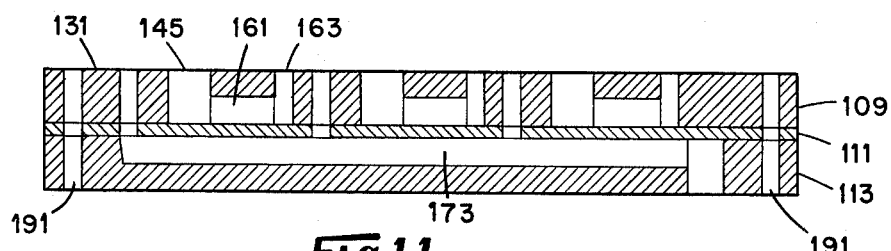
FIG. 11 is a sectional view taken on line 11—11 in FIG. 5.
Figure 5:
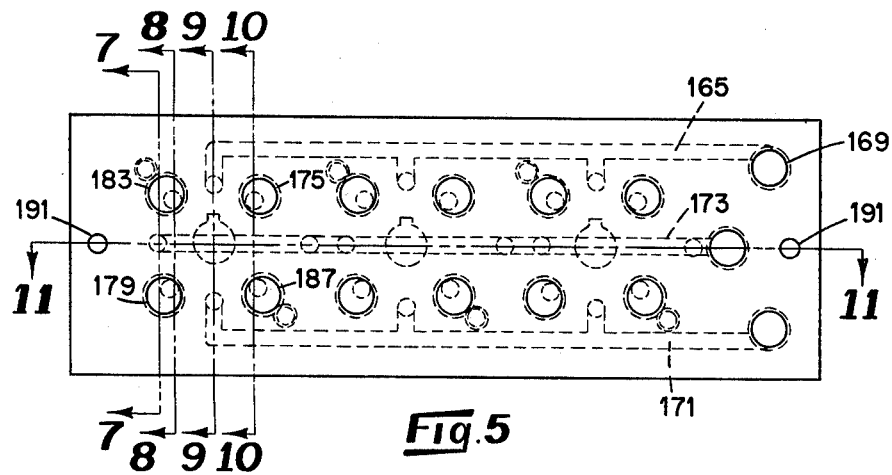
FIG. 5 is a plan view of the assembled manifold shown in FIG. 4.

As shown in FIG. 11, a channel 161 is provided connecting the pilot air inlet 145 with a pilot air exhaust port 163 in the mounting face 131.

The middle section 11 of the manifold 15 is provided with a plurality of openings between the mounting section 109 and the face section 113 and otherwise seals the pilot channels 161 formed in the mounting section 109. Opening 133' is positioned to correspond to drive air outlet 133. Opening 135' is positioned to correspond to drive air inlet 135. Opening 137' is positioned to correspond to chip air outlet 137. Opening 139' is positioned to correspond to chip air inlet 139. Opening 143' is positioned to correspond to water inlet 143. Opening 145' is positioned to correspond to pilot air outlet 145.

The face section 113 includes a drive air channel 165 in its inner surface, one end of channel 165 being connected to both a passageway 167 in the mounting section 109 and middle section 111 and a passageway 169 in the face section 113. Passageway 167 is connected to conduit 75. Passageway 169 is connected to conduit 77. The drive air channel underlies only the openings 133', 133a' and 133b' and thus provides communication between the conduit 75 and the drive air valve inlets 115, 115a (not shown) and 115b (not shown).

Also included in the inner surface of the face section 113 is a chip air channel 171, one end of the channel 171 being connected to the chip air inlet 91. The chip air channel 171 underlies only the openings 137', 137a', and 137b' and thus provides communication between the conduit 85 and the chip air valve inlets 119, 119a (not shown) and 119b (not shown).

Also included in the inner surface of the face section 113 is a water channel 173, one end of the channel 173 being connected to the water inlet 99. The water channel 173 underlies only the openings 141', 141a', and 141b' and thus provides communication between the conduit 93 and the water inlets 123, 123a (not shown) and 123b (not shown). Additionally, the face section 113 is provided with a passageway 175 connecting opening 135' to a drive air exit 177, a passageway 179 connecting opening 143' to a water exit 181, a passageway 183 connecting opening 139' to a chip air exit 185 and a passageway 187 connecting a pilot air entrance 189 to opening 145'. The passageways 175, 179, 183 and 187 are preferably threaded to accept a mating threaded nipple for conduit connections.

Extending through all three sections 109, 111 and 113 are a pair of mounting bores 191 for mounting the manifold assembly.

The layers 109, 111 and 113 are preferredly composed of a clear plastic, such as Lexan and sealingly joined by a heat-welding process well known in the art. Clarity of the material allows easy recognition of any obstructions which may by chance develop in the manifold 15.

The base plate 112 of the valve 25 is sealingly engaged against the mounting face 131 of the mounting section 109 of the manifold 15 by means of the mounting screws 157. A suitable gasket (not shown) is preferably interposed between the faces of the base plate 112 of the valve 25 and the mounting face 131 of the mounting section 109 of the manifold 15 to insure a pressure tight connection.

The valve 25 includes an elongated cylindrical housing 193 having an internal, axial, central passageway 195 defined by a cylindrical wall 197. One end of the housing 193 is attached to the base plate 112 and the other end of the housing is provided with an end cap 199 which seals the outer end of the passageway 195. Disposed within the passageway 195 is a spool assembly 200. The spool assembly 200 includes a shaft 201, of relatively small diameter, having an axially extending central opening 203. The shaft 201 also is provided with four, integral, spaced-apart enlargements 204, 205, 206, and 208, each of which has a circular cross section which approaches the diameter of the passageway 195. Sealing means 207 are provided between each of the enlargements and the side wall 197 of the passageway 195 to divide the passageway into three sealed annular compartments 209, 210 and 212. The sealing means 207 on each of the enlargements 204, 205, and 206 each include a pair of spaced apart seals 207' which provide a sealed chamber 214 of small volume which is isolated from the adjacent compartment. A single seal 207' is privided on the enlargement 208. The seals are desirably provided by O-rings or the like.

The length of the shaft 201 is less than the length of the passageway 195 so that the shaft, with its associated enlargements 204, 205, 206 and 208 can move longitudinally within the passageway 195. A compression spring 211 is disposed in the passageway 195, one end of the spring 211 bearing upon a shoulder 213 on the base plate 112 and the other end of the spring 211 bearing upon the enlargement 208. Thus, the spring 211 normally biases the spool assembly 200 away from the base 112.

In order to move the spool assembly 200 towards the base 112, pilot air (the sorce of which will be hereinafter described) is conducted from the inlet 127 in the base plate 112, through a passageway 216 in the wall 197 of the housing 193 through an inlet 218 to a space 221 between the cap 199 and the enlargement 204, the enlargement most remote from the base. This builds up air pressure in the space 221 which acts upon a piston surface 223 provided by the enlargement 204 to move the spool assembly 200 towards the base plate 112. It will be noted that the central opening 203 in the shaft 201 is connected through the outlet 129 on the base plate 112 through the channel 161 to the exhaust port 163. In order that pressure builds up in the space 221 between the cap 199 and the enlargement 205, the diameter of the central opening 203 is sufficiently small to provide a back pressure which results in the necessary pressure build-up to overcome the biasing action of the spring 211.

Included within the housing 193 is a passageway 225 connecting the drive air inlet 115 in the base plate 112 to a drive air wall inlet 227, a passageway 228 connecting a drive air wall outlet 229 to the drive air outlet 117 in the base plate 112, a passageway 231 (FIG. 3B) connecting the chip air inlet 119 in the plate to a chip air wall inlet 233 (FIG. 3B), a passageway 235 connecting a chip air wall outlet 237 to the chip air outlet 121 in the base plate, a passageway 239 connecting the water inlet 123 in the base plate 112 to a water wall inlet 241 and a passageway 243 connecting a water wall outlet 244 to the water outlet 125 in the base plate.

Figures 3, 3A, 3B:
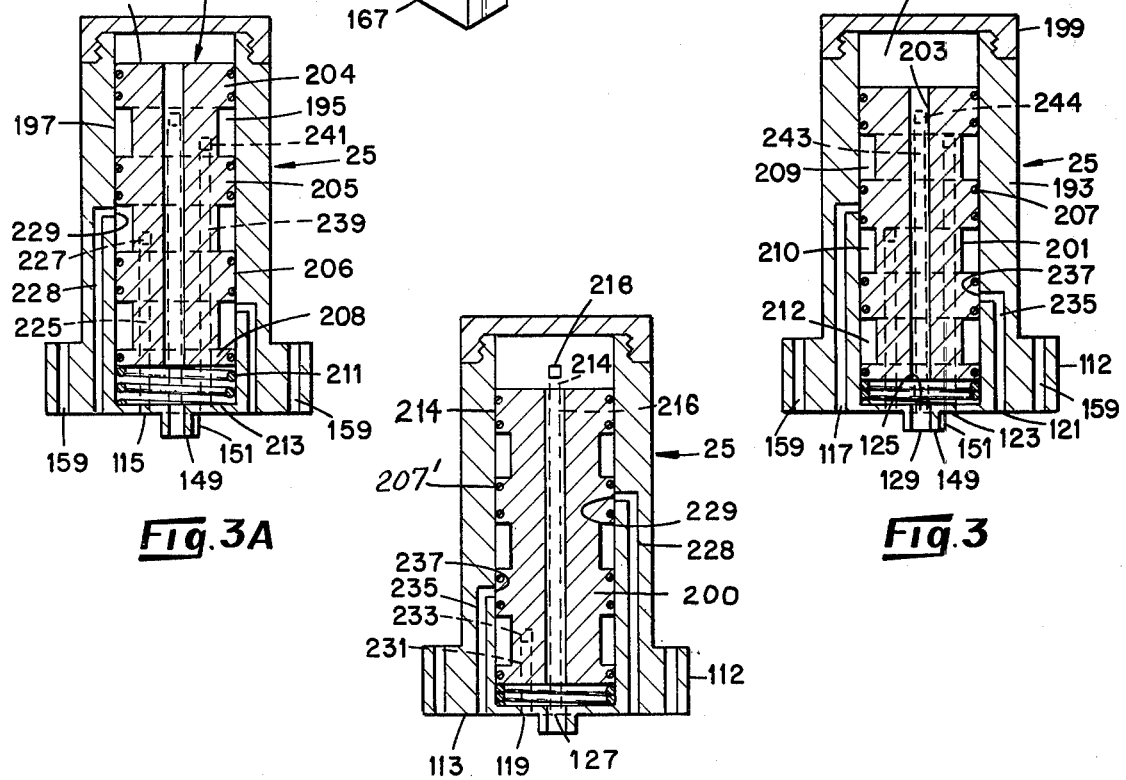
FIG. 3 is a sectional view taken on line 3—3 in FIG. 1 of a replaceable valve assembly unit, the valve being in the closed position.
FIG. 3A is a sectional view taken on line 3—3 in FIG. 1 of a replaceable valve assembly unit, the valve being in the open position.
FIG. 3B is a sectional view taken on line 3B—3B in FIG. 1 of a replaceable valve assembly unit, the valve being in the closed position.
Figure 6:
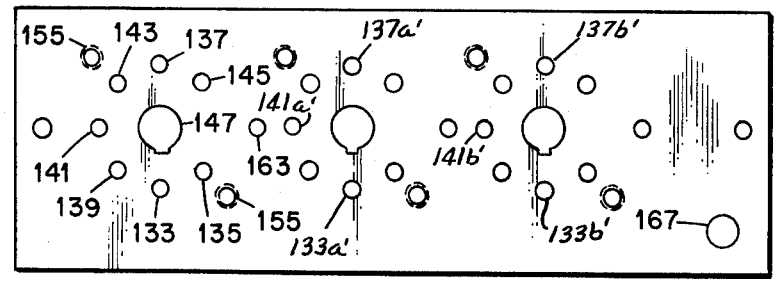
FIG. 6 is a plan view of the face of the manifold shown in FIG. 5 which is adapted to receive the replaceable valve assembly units.
Figure 7:
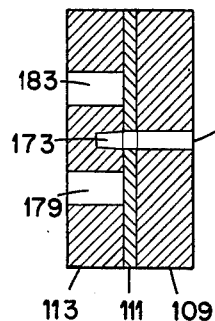
FIG. 7 is a sectional view taken on line 7—7 in FIG. 5.
Figure 8:
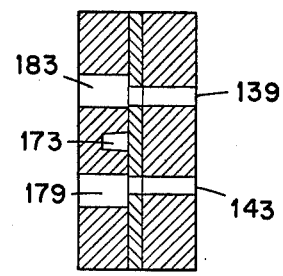
FIG. 8 is a sectional view taken on line 8—8 in FIG. 5.
Figure 9:
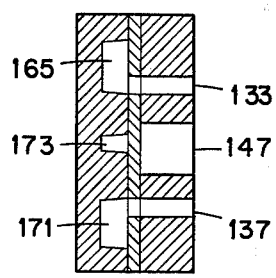
FIG. 9 is a sectional view taken on line 9—9 in FIG. 5.
Figure 10:
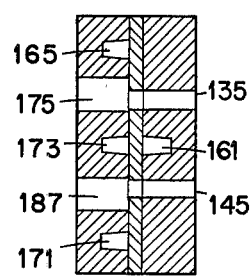
FIG. 10 is a sectional view taken on line 10—10 in FIG. 5.

The wall inlets and wall outlets for drive air, chip air and water described above are positioned along the wall 197 as illustrated in FIGS. 3, 3A and 3B. It will be noted that the drive air wall inlet 227 and wall outlet 229 are spaced along the axis of the passageway 195 a distance such that when the spool 200 is in its position remote from the base plate 112, the inlet 227 and outlet 229 are in communication through the compartment 210. However, when the spool 200 is biased towards the base plate 112 by the action of pilot air the inlet 227 is in communication with the compartment 210 and the outlet 209 is in communication with the chamber on the enlargement 205, thus isolating the inlet and outlet one from the other.

The chip air wall inlet 233 and chip air wall outlet 237 are similarly positioned with respect to compartment 212 and the annular chamber surrounding enlargement 206.

The water wall inlet 241 and water wall outlet 244 are similarly positioned with respect to compartment 209 and the annular chamber surrounding enlargement 204.

Figure 2:
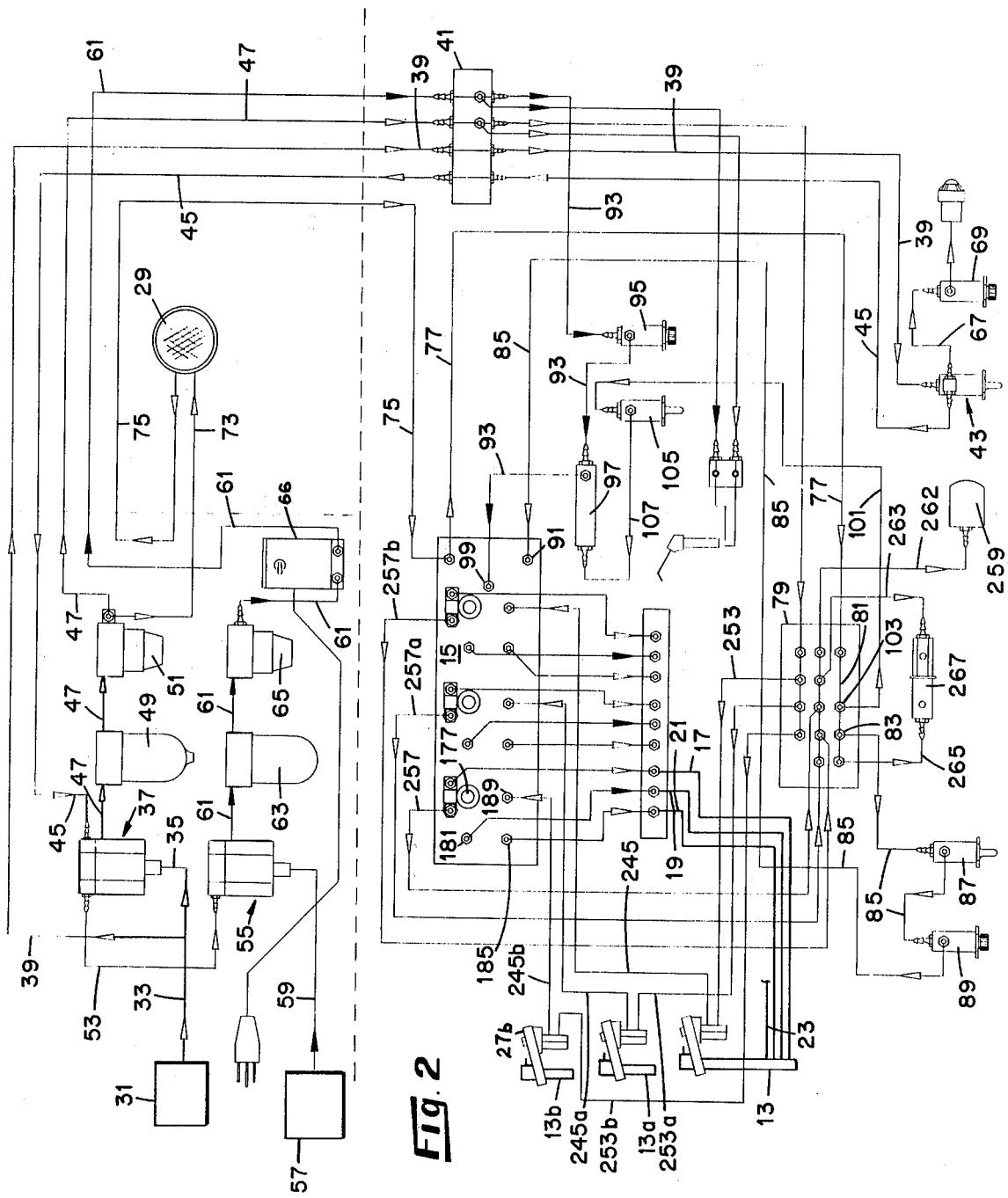
FIG. 2 is a schematic flow diagram of the control system for controlling three separate tools.
Figure 4:
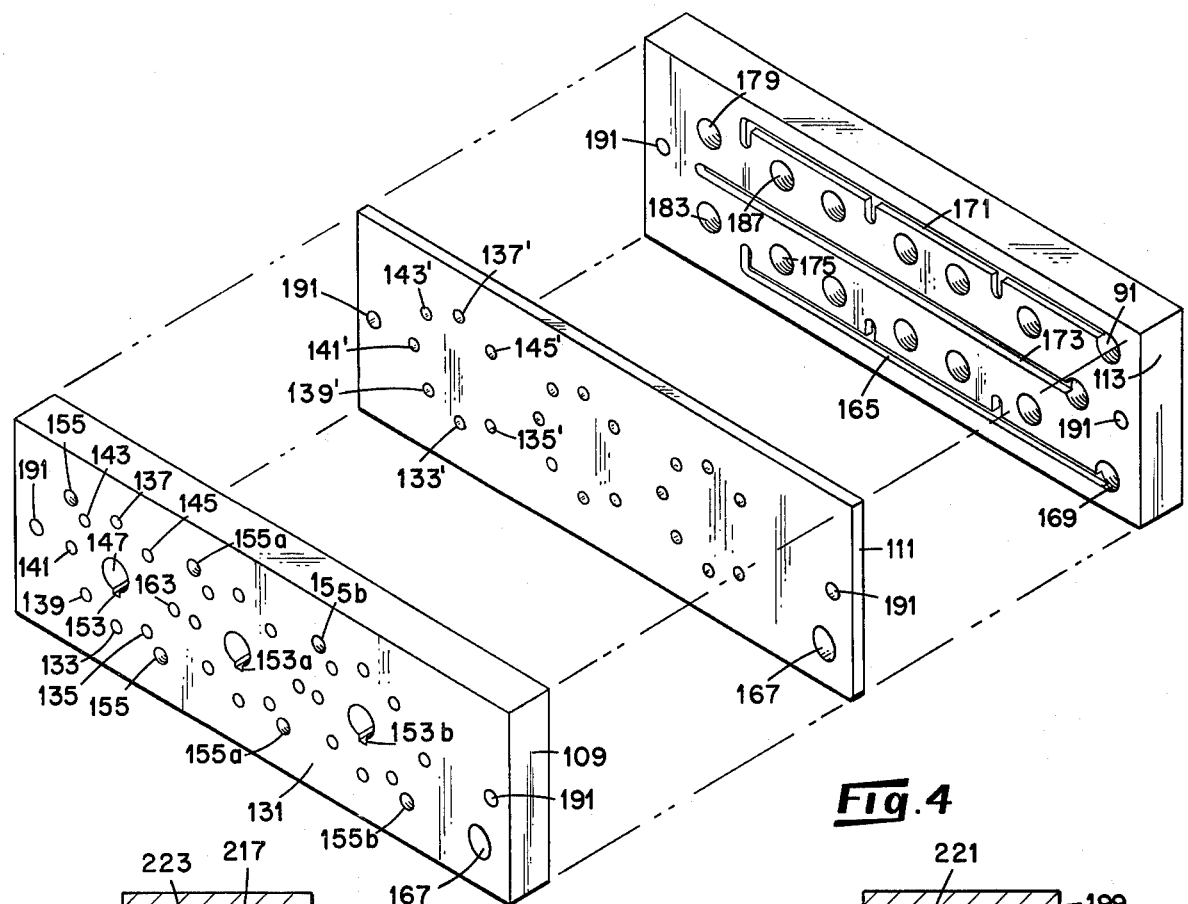
FIG. 4 is an exploded perspective view of the manifold which is a part of the control means shown in FIG. 1.

Connected to the drive air outlet 177 is a regulator 255 which may be set to determine the maximum drive air pressure available for a particular tool. As illustrated, conduit 17, which supplies drive air to the drill 13, is connected to the regulator 255. Also connected to the regulator, through conduit 257, is an air gauge 259. Conduit 257 is connected at the distribution box 79 to an internal passageway 261 which is connected to a conduit 262 which connects to the air gauge 259. As shown in FIG. 2, all tool stations are similarly connected to the pasageway 261 at the distributor box 79. The air gauge 259 thus provides a visual measure of the pressure of drive air supplied to the tool which is in use.

Also connected to passageway 261 and passageway 81 in the distributor box 79 are conduits 263 and 265, respectively, which are in turn connected to a normally open relief valve 267. Relief valve 267 normally vents to the atmosphere all drive air, chip air and water control air conduits between the foot pedal 29 and the valve 25. The relief valve is closed when the foot pedal is activated to allow drive air flow from conduit 73 into conduit 75.

A particularly useful type of valve to use for the air actuated water valve 97 is one which includes an "anti-syphon" feature to prohibit dripping after water flow is stopped. Such valves are available commercially.

In operation, the above described system provides a flexible means to control the operation of a dental or surgical drills. As has been pointed out, the usual installation includes a plurality of drills or other tools such as the tools 13, 13a, and 13b, as shown in FIG. 2. Each of these tools is adjusted to provide the proper operating speed for a given job by preadjusting the regulators 255, 255a or 255b, as required, and each of the proper bits are placed in each of the tools prior to operating on a patient. In order to supply the system the master valve 43 is turned on supplying drive air, chip air and water or other liquid to the manifold 15, the valve 87, and the valve 97, respectively, in the manner which has been described. The dentist or surgeon then determines whether he will require chip air or water for the operation of the tool and presets this condition through the valve 105 for water and the valve 87 for chip air.

As has been pointed out above, when the unit is in the ready condition, pilot or control air is flowing through each of the spool valves 25, 25a, and 25b to maintain the spool in a position adjacent its respective base plate 112, 112a and 112b, thereby preventing flow to any of the tools, as shown in FIGS. 3 and 3A. Assuming that the operator chooses to use tool 13, he lifts it from its associated hanger 27 which blocks the flow of control air to only the associated spool valve 25. Control air continues flowing to spool valves 25 and 25b, maintaining their closed positions. As soon as the supply of control air to the valve 25 is interrupted the spring 211 causes the spool to move axially in the passageway 195 which movement simultaneously provides a supply of drive air, and chip air and/or water as selected, to the tool 13 upon actuation of the foot pedal 29. When the foot pedal 29 is released the supply of drive air, water and chip air to the tool is stopped and the air pressure in the system going to the tool is vented through the relief valve 267. Replacement of the tool 13 back on its hanger 27 causes control air to again flow through the passageway in the spool valve 25, causing the spool to move against the pressure of the spring 211 thereby closing off simultaneously the supply of both air and liquid to the tool. It is obvious that if the capacity of the various conduits is of the proper size, more than one tool can be run at a time. However, in the illustrative embodiment of the invention each tool would be supplied with the same selected combination of chip air and water.

In the event that the system malfunctions in any way it is relatively easy to service. The provision of the transparent manifold makes it possible to visually examine all of the interior passages of the manifold to determine the location of any points at which it may be blocked. Also, the provision of the spool valves 25, which simultaneously control the multiple supplies to each tool may be readily dismounted by removing the mounting screws 157 and replacing the valve unit 25 with another one of the same construction. Since the position of the valve is keyed to a given position on the mounting face of the manifold through the boss 149 and the key 151 it is apparent that there is no possibility for misconnecting any fluid lines. It has been determined that with an integral valve unit and manifold of the type described that the replacement of a valve can be accomplished in but a few minutes thereby insuring that there is a minimal chance of any tool being out of service for more than a short period of time.

While a preferred embodiment has been shown and described, it will be understood that there is no intent to limit the invention by such disclosure, but rather, it is intended to cover all modifications and alternate constructions falling within the spirit and scope of the invention as defined in the appended claims.

What is claimed is:

1. A system for supplying a plurality of tools with drive air, low pressure air and liquid from sources of the same, including a plurality of valve sets, each set being enclosed in an individual housing and adapted for individual activation by control air and associated with one of said tools, each of said valve set housings having a valve mounting face, a fabricated unitary manifold having a mounting face to which the mounting faces of the plurality of individual valve housings are detachably connected, each valve being operable to simultaneously supply drive air, low pressure air and liquid to its associated tool in response to a predetermined condition of control air, said mounting face on each valve set housing having an inlet and outlet for each of drive air, low pressure air, liquid, and control air, said inlets and outlets being arranged in a predetermined pattern, a set of openings in said mounting face of said manifold for each of the mounting faces of said valve set housings, said openings in each set corresponding to the inlets and outlets in the mounting face of each said valve set housing, mating means for mounting the mounting face of each of said housings on the mounting face of said manifold with the respective inlet and outlet openings in registration, conduit means separately supplying drive air, low pressure air and liquid from said sources of the same to said manifold, a common passageway in said manifold connecting said drive air supply conduit to the openings in the manifold mounting face which correspond to the drive air inlets in each of said valve mounting faces, a common passageway in said manifold connecting said low pressure air supply conduit to the openings in the manifold mounting face which correspond to the low pressure air inlets in each of said valve mounting faces, a common passageway in said manifold connecting said liquid supply conduit to the openings in the manifold mounting face which correspond to the liquid inlet in each of said valve mounting faces, a hanger for each tool having a control air inlet and outlet, conduit means from the control air source to the control air inlet of each said hanger, conduit means connecting the control air outlet of each said hanger to said manifold, means in said hanger actuated by the support of said tool by said hanger to connect said control air inlet and control air outlet, individual passageways in said manifold connecting each said control air supply conduit means from each hanger to the opening in the manifold mounting face which corresponds to the control air inlet for the valve set housing associated with that hanger, passageways connecting the openings in the manifold mounting face which correspond to the control air outlet in each of said valve mounting faces to the atmosphere, individual conduits supplying drive air, low pressure air and liquid from the manifold to each of said tools, an individual passageway in said manifold connecting each opening in the manifold mounting face which corresponds to the drive air outlet in each valve mounting face to the associated drive air supply conduit to the tool associated with that valve set, an individual passageway in said manifold connecting each opening in the manifold mounting face which corresponds to the low pressure air outlet in each valve mounting face to the associated low pressure air supply conduit to the tool associated with that valve set, and an individual passageway in said manifold connecting each opening in the manifold mounting face which corresponds to the liquid outlet in each valve mounting face to the liquid supply conduit to the tool associated with that valve set, each said valve set comprising a spool-valve comprising a spool which includes a central elongated shaft having axially spaced apart cylindrical enlargements thereon which have a diameter greater than said shaft, said housing for said valve set having walls defining a passageway proportioned to receive said cylindrical enlargements and means for providing a fluid-tight seal between the walls of said passageway and said cylindrical enlargements, said inlet for drive air in said valve mounting face communicating with said passageway, and said outlet for drive air in said valve mounting face communicating with said passageway, said points of communication with said passageway for said drive air inlet and outlet being positioned so that longitudinal movement of said spool in said passageway prevents or permits passage of drive air between said drive air inlet and outlet, said inlet for low pressure air in said valve mounting face communicating with said passageway, said outlet for low pressure air in said valve mounting face communicating with said passageway, said points of communication with said passageway of said low pressure air inlet and outlet being positioned so that longitudinal movement of said spool in said passageway prevents or permits passage of low pressure air between said low pressure air inlet and outlet, said inlet for liquid in said valve mounting face communicating with said passageway, said outlet for liquid in said valve mounting face communicating with said passageway, said points of communication with said passageway of said liquid inlet and said outlet being positioned so that longitudinal movement of said spool in said passageway permits or prevents passage of liquid between said liquid inlet and outlet, each of said inlets being sealed by said sealing means from each of said inlets and each of said outlets other than its related outlet, the proportions of said cylindrical enlargements and positions of said points of communication of said inlets and outlets of said drive air, low pressure air, and liquid with said passageway being such that longitudinal movement of said spool simultaneously permits or prevents flow of said drive air, low pressure air and liquid through said passageway of said spool valve to the associated tool and means connecting the control air inlet in each of said valve set housings to a portion of said passageway in said housing to effect longitudinal movement of said spool.

* * * * *